| United States Patent [19] | [11] | 4,100,172 |
|---|---|---|
| Mui et al. | [45] | Jul. 11, 1978 |

[54] SULFUR CONTAINING NORBORNANYL SILICON COMPOUNDS

[75] Inventors: Jeffrey Y. P. Mui, Ossining; Bernard Kanner, West Nyack, both of N.Y.

[73] Assignee: Union Carbide Corporation, New York, N.Y.

[21] Appl. No.: 694,028

[22] Filed: Jun. 7, 1976

Related U.S. Application Data

[63] Continuation of Ser. No. 187,551, Oct. 7, 1971, abandoned.

[51] Int. Cl.$^2$ .............................................. C07F 7/08
[52] U.S. Cl. ..................... 260/327 H; 260/448.2 N; 260/448.8 R
[58] Field of Search ................... 260/327 H, 448.8 R, 260/448.2 N

[56] References Cited

U.S. PATENT DOCUMENTS

| 3,586,700 | 6/1971 | Kurtz et al. | 260/327 |
| 3,768,537 | 10/1973 | Hess et al. | 152/330 |

OTHER PUBLICATIONS

Shields et al., Journal of the American Chemical Society, 91:19 (9-10-69) pp. 5415 and 5416.

*Primary Examiner*—Richard L. Raymond
*Attorney, Agent, or Firm*—Reynold J. Finnegan

[57] ABSTRACT

The invention relates to novel sulfur substituted norbornyl silicon compounds. Illustrated are trithianyl, dimercapto and mono-mercapto substituted norbornylsilicon compounds.

10 Claims, No Drawings

SULFUR CONTAINING NORBORNANYL SILICON COMPOUNDS

This is a continuation of our prior U.S. application Ser. No. 187,551, filed Oct. 7, 1971, now abandoned.

This invention relates to new sulfur substituted norbornyl substituted silicon compounds. More particularly, this invention relates to the novel sulfur substituted norbornyl silicon compounds characterized by having present therein the following structure:

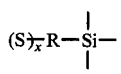

wherein the free valences of the silicon atom are bonded to one or more of monovalent hydrocarbon groups, hydrolyzable groups or oxygen which in turn is bonded to another silicon atom whereby to form a siloxane, R is one of the polyvalent cycloaliphatic hydrocarbon radicals characterized as follows:

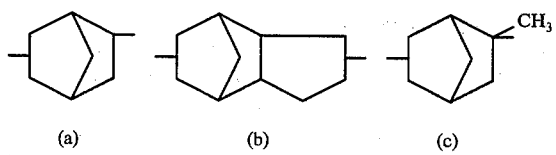

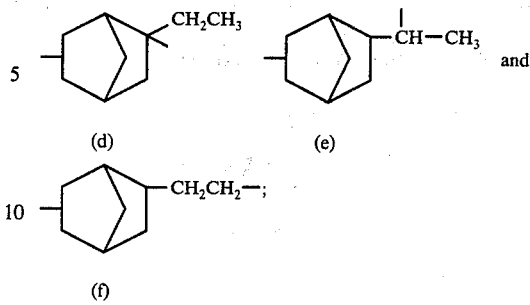

$x$ has the value of 1, 2 or 3; provided that when $x$ is 1 or 2 each sulfur atom is bonded to hydrogen to form a mercaptan, and when $x$ is 2, the two mercaptans are attached to separate carbon atoms and such carbon atoms are adjacent to one another (or vicinal to each other), and when $x$ is 3, the sulfur atoms form a trisulfide wherein each sulfur atom is bonded to another sulfur atom and the terminal valences of the trisulfide are bonded to vicinal carbon atoms.

The sulfur substituted cycloaliphatic compounds of this invention as characterized by the formula I above, can be produced by the reaction of a sulfur compound with an unsaturated precursor of the silicon compound. Such unsaturated precursors are characterized in the table below, wherein the monovalent hydrocarbon substituted radical which is employed for formation of R is depicted as the reaction of a cycloaliphatic compound with a silicon compound to produce the desired precursor product:

-continued

| (S)$_x$R—Si— | X—Si≡ wherein X is | Cycloaliphatic Compound | Process | Silicon Product (R'—Si—) |
|---|---|---|---|---|
| (e) | H— | 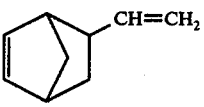 | addition catalyst | 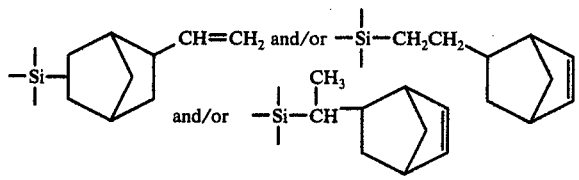 |
| (f) | H— | 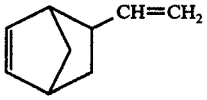 | addition catalyst | SAME AS (e) IMMEDIATELY ABOVE |

The addition reactions characterized in the preceding table for the manufacture of the unsaturated cycloaliphatic silicon compounds which are employed as starting materials in making the sulfur substituted compounds of this invention, are common reactions in the art and involve, where characterized in the above table where heat alone is employed, the well-known Diels-Alder addition reaction and, where characterized as employing an addition catalyst, the well-known addition reaction by use of platinum catalysis. The Diels-Alder reaction involves simply mixing the cycloaliphatic compound characterized above plus the silicon compound and heating the mixture to a temperature of from about 75° C. to about 225° C., preferably from about 100° C. to about 200° C. When effecting the addition process by platinum catalysis, the reaction may be effected neat or in the presence of a solvent at temperatures of about room temperature (e.g., 20–25° C.) to about 150° C.

The platinum catalyst employed in effecting the addition reaction characterized above in the table, may be any of the known platinum catalysts used by the art, such as platinum deposited on alumina or carbon black, chloroplatinic acid, platinum-olefin complexes and platinum complexes with other ligands such as the known nitrile ligands, amine ligands and phosphine ligands. In carrying out such a catalysis reaction, one normally employs from about 10 to about 100 parts per million of platinum, based on the weight of the reactants.

When carrying out the addition reaction by platinum catalysis, one may employ a solvent. The usual solvents may be employed, such as the hydrocarbon solvents, preferably the aromatic hydrocarbon solvents, ether solvents, alcohol solvents, and the like.

The unsaturated cycloaliphatic silicon compounds characterized above are treated with sulfur compounds to form the desired sulfur substituted silicon compounds of this invention. Basically, three procedures are employed for producing these sulfur substituted silicon compounds. The first process involves the reaction of elemental sulfur with the unsaturated cycloaliphatic silicon compound. This results in the formation of the trithiane substituted cycloaliphatic silicon compound. The second process involves hydrogenation of the trithiane substituted cycloaliphatic silicon compound to produce a dimercapto substituted cycloaliphatic silicon compound. The third process involves the treatment of the unsaturated cycloaliphatic silicon compound with hydrogen sulfide ($H_2S$). This produces a mono-mercapto substituted cycloaliphatic silicon compound.

In order to more definitively illustrate this point, reference is made to the following table which illustrate the various procedures described above with respect to specific unsaturated cycloaliphatic silicon moieties:

| Starting Silicon Compound | Sulfur Treatment | Mercapto Treatment | Final Sulfur Substituted Product |
|---|---|---|---|
| 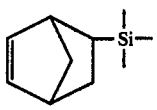 | Sulfur | — | 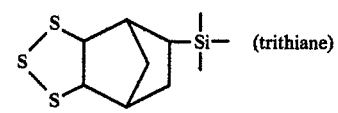 (trithiane) |
| 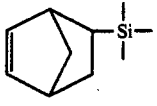 | Sulfur | Hydrogenation | 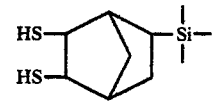 |
| 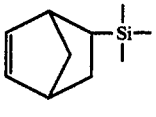 | — | $H_2S$ | 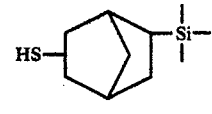 |
| 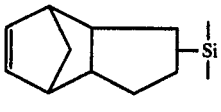 | Sulfur | — | 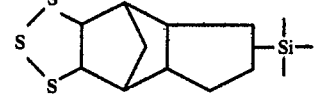 |

-continued
| Starting Silicon Compound | Sulfur Treatment | Mercapto Treatment | Final Sulfur Substituted Product |
|---|---|---|---|
| " | Sulfur | Hydrogenation | 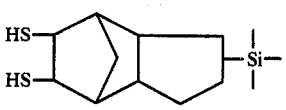 |
| " | — | $H_2S$ | 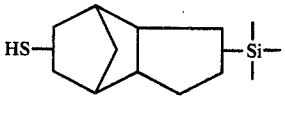 |
| 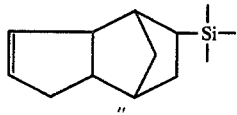 | Sulfur | — | 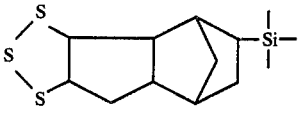 |
| " | Sulfur | Hydrogenation | 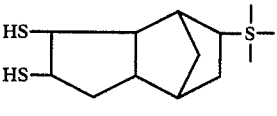 |
| " | — | $H_2S$ | 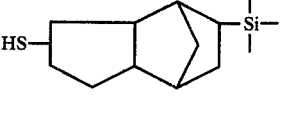 |
| 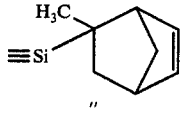 | Sulfur | — | 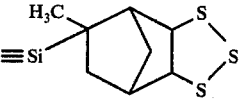 |
| " | Sulfur | Hydrogenation |  |
| " | — | $H_2S$ | 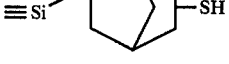 |
| 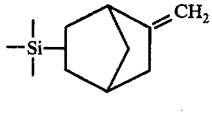 | — | $H_2S$ | 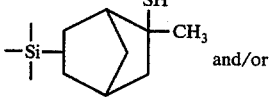 and/or 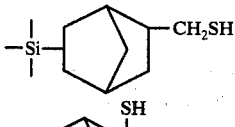 |
| 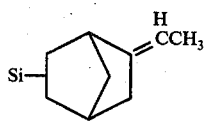 | — | $H_2S$ | 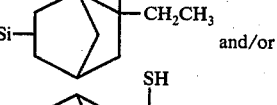 and/or 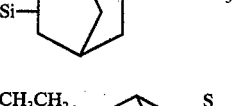 |
| 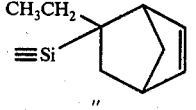 | Sulfur | — | 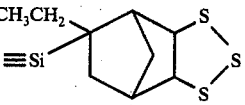 |
| " | Sulfur | Hydrogenation |  |
| " | — | $H_2S$ | 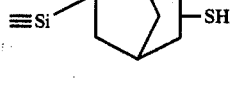 |

| Starting Silicon Compound | Sulfur Treatment | Mercapto Treatment | Final Sulfur Substituted Product |
|---|---|---|---|
| ![norbornyl-vinyl silane] | — | H₂S | ![norbornyl-CH₂CH₂SH and/or CH(SH)CH₃ silane] and/or |
| ![-Si-CH₂CH₂-norbornene] | Sulfur | — | ≡SiCH₂CH₂-norbornyl-S-S-S cyclic |
| " | Sulfur | Hydrogenation | ≡SiCH₂CH₂-norbornyl-SH, SH |
| " | — | H₂S | ≡SiCH₂CH₂-norbornyl-SH |
| ![-Si-CH(CH₃)-norbornene] | Sulfur | — | -Si-CH(CH₃)-norbornyl-S-S-S cyclic |
| " | Sulfur | Hydrogenation | -Si-CH(CH₃)-norbornyl-SH, SH |
| " | — | H₂S | -Si-CH(CH₃)-norbornyl-SH |

The starting silicon compound, characterized above as X—Si≡, may be any silicon compound containing the X radical as defined above, that is, vinyl or hydrogen, which is in a non-gelled or non-infusable state. Thus, the starting silicon compound can be a silane, a cross-linked siloxane, and a linear siloxane of variant molecular weight from a dimer to a highly viscous gum. The siloxane may be a homopolymer wherein all of the silicon atoms thereof contain a X bonded thereto or a copolymer in which some of the radicals contain a X bonded thereto. When the sulfur substituted cycloaliphatic silicon compound is in the form of a silane, that is a compound which contains only 1 silicon atom therein, there should be bonded to the silicon atom at least one of the aforesaid sulfur substituted cycloaliphatic moieties. In addition, the silane silicon atom should have bonded to it at least one hydrolyzable radical, such as chlorine, alkoxy (e.g., methoxy, ethoxy, n-propoxy, isopropoxy, n-butoxy, methoxy- or ethoxyethoxy, beta-chloropropoxy, beta-chloroethoxy, and the like) acetoxy, and the like. The silane may contain up to three of such hydrolyzable groups. Also, the silane may contain a monovalent organic group bonded to the silicon atom by a carbon-to-silicon bond. Illustrative of such organic radicals are monovalent hydrocarbon radicals such as methyl, ethyl, n-propyl, n-hexyl, phenyl, 1- or 2-naphthyl, as well as the other well-known monovalent hydrocarbon radicals typically employed in silanes. Thus, the silane encompassed by this invention can contain from 1 to 3, inclusive, sulfur substituted cycloaliphatic moieties bonded to Si, at least one and up to three hydrolyzable groups, and 0, 1 or 2 monovalent organo radicals other than the sulfur substituted cycloaliphatic moieties bonded to Si by carbon to silicon bonds.

The starting siloxane compounds for making the sulfur substituted products of this invention are characterized by the presence in the molecular structure thereof of the radical

Organo polysiloxanes are characterized as polymers which contain silicon bonded to silicon through an oxygen atom and can contain up to an average of 3 organo groups (bonded to Si by a carbon to silicon bond) per Si therein. When the polymer contains 3 organo groups per Si, the resulting siloxane is characterized as a disiloxane. The organo to Si ratio of a siloxane characterizes whether that polymer can be a very low molecular weight dimer, as described above, or a high molecular weight linear polymer, which occurs when the organo Si ratio is 2, or a cross-linked complex siloxane network which is typically present when the organo to Si ratio is below 2 down to about 0.5. The latter organo to Si ratio, that is an organo to Si ratio which is less than 2, is typically referred to as a siloxane resin. When the organo to Si ratio is approximately 2, the product can be an oil up to a high molecular weight viscous gum used in the manufacture of silicone rubber. The sulfur substituted cycloaliphatic siloxanes of this invention can possess any of the aforementioned organo to Si ratios. Indeed, all of the organo groups can be of the sulfur substituted cycloaliphatic moieties described herein. However, it is preferred that only a portion of the organo moieties bonded to silicon of siloxane are sulfur substituted cycloaliphatic moieties as described herein. Typically, it is desirable that not more than about 50 mole percent of the organo moieties of the siloxane are the sulfur substituted cycloaliphatic type. In most cases, not more than about 20 mole percent of the organo moieties will be of the sulfur substituted cycloaliphatic type described herein. The remaining organo moieties bonded to the silicon may be any of the aforementioned monovalent hydrocarbons such as depicted above, including as well, vinyl, and non-organo groups such as hydrogen which is directly bonded to silicon to form the silicon hydride moiety. There may also be present as organo groups bonded to Si in such copolymers, organo functional moieties. For example, one might also have present amino organo groups such as gamma-aminopropyl, delta-aminobutyl, gamma-aminoisobutyl, beta-N-aminoethyl-gamma-aminopropyl, epoxy substituted radicals such as gamma-glycidyloxypropyl, beta-3,4-epoxycyclohexylethyl, 3,4-epoxy-n-butyl, and the like, acryloxy radicals such as gamma-methacryloxypropyl, gamma-acryloxypropyl, gamma-methacryloxyisobutyl, and the like.

The sulfur substituted cycloaliphatic silicon compounds of this invention have a variety of utilities. The silanes described above containing 1 to 3 hydrolyzable groups, preferably 3 hydrolyzable groups, are very useful as coupling agents in that they enhance the adhesion of unsaturated resinous materials to a variety of substrates. These silanes may be used directly on the substrate as a primer or may be incorporated in the unsaturated resin to form an integral blend which may be supplied to the substrate whereby, after applying heat, the coupling agent effect is noted in that the silane migrates to the surface of the substrate to be bonded thereto and to also be bonded to the resin through reaction of the sulfur functionality with the unsaturation of the resin. Such silanes may be employed in very small quantities to effect this coupling action. For example from about 0.25 up to 2 weight percent, basis the weight of the resin, may be supplied either as a primer to the substrate or directly into the resin. The sulfur substituted silicon compounds of this invention, whether a silane or siloxane, can be employed in the cure of unsaturated resins and elastomers in order to effect crosslinking thereof. The mercapto substituted products of this invention possess the ability to accellerate the cure of an elastomer such as a copolymer of butadiene and styrene, neoprene, butadiene-acrylonitrile copolymers, and the like. The siloxane oils or fluids containing the sulfur substituted cycloaliphatic radicals bonded thereto may be employed as lubricants, particularly to effect lubrication where metal is contacting metal, as an additive to conventional hydrocarbon oils to enhance the lubricity thereof as a lubricating fluid, as a lubricating fluid in brake systems, as a emulsifiable component with water to be utilized in the separation of polyvalent metals and monovalent metals from water bodies, as a compatible resinous material for combination with elastomers whereby to effect improvement in temperature resistance, bonding to metals and siliceous fibers and pigments or fillers, and the like.

In order to provide more specific illustrations of this invention, reference is made to the following examples. It is not intended that these examples act in any way to limit the scope of this invention. They are provided solely for the purpose of illustrating this invention.

EXAMPLE I

Into a 2-liter three-necked flask equipped with a mechanical stirrer, a condenser and a thermometer were charged 1230 grams of N,N-dimethyl formamide (DMF) and 236 grams of sulfur flower. The contents were stirred and ammonia gas from a cylinder was bubbled into the mixture at 61 ml/min for 20 min. (total 1220 ml or 0.49 mole). Then, 491.5 grams (2.29 mole) of trimethoxynorbornenyl-silane,

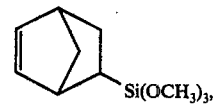

were added and the contents were heated to 110° for 2 hours. V.P.C. analysis showed > 99% of the

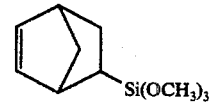

had been reacted. The contents were cooled to 60° and the solvent, DMF, was stripped under vacuo. Essentially quantitative recovery of DMF (1228 g) was observed. Weight of crude product was 724 grams, amounting to ca. 100% yield of

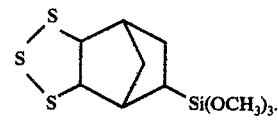

A sample of the crude (64.5 g) was distilled at 0.0005 mm Hg at 120° C. A light yellow liquid (58.8 g) was collected. The distilled product has the following properties:

$\eta^{25} = 1.5702$

Elemental Analysis = Calculated for $C_{10}H_{18}$—$O_3S_3Si$; C, 38.68; H, 5.84; S, 30.98; Si, 9.04; MW, 310.5. Found C, 37.71; H, 5.79; S, 29.18; Si, 8.62; MW, 323; IR and NMR spectrum are in agreement with the proposed structure

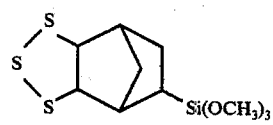

Yield = 91.3%

EXAMPLE II

Into a 300-ml high pressure reactor were charged 0 grams of crude

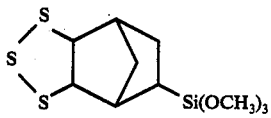

from Example I, 30 ml. of methanol and 0.64 grams of rhenium heptasulfide, and heating was carried out at 120°–130° C. for 2½ hours. Excess gas was vented and products were collected in a small bottle. Distillation yield a fraction (61) grams, b.p. 115° C./0.1 mmHg, of colorless liquid, $\eta^{25}=1.5203$. IR and NMR spectra were in agreement with the structure of

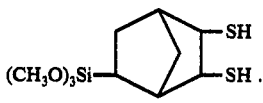

Titration of the distilled product with standard iodine solution showed the presence to two —SH groups.

Elemental Analysis = Calculated for $C_{10}H_{20}O_3S_2Si$ C,42.82; H, 7.19; S, 22.86; Si, 10.00. Found = C, 43.64; H, 7.30; S,22.50; Si,9.85 Yield of distilled

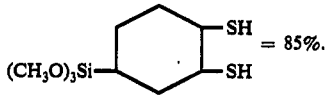

EXAMPLE III

Into a 300-ml high pressure reactor were charged 143.5 grams of

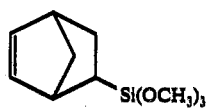

and 0.42 grams azobisisobutyronitrile catalyst. Condensed hydrogen sulfide, 106 ml, were transferred into the reactor and the contents were heated to 90° C. for 2½ hours. Excess $H_2S$ was destroyed by venting to a scrubber. The crude products, 162 grams, were distilled and a fraction, b.p. 82° C. at 2mm. weighing 137.5 g, was collected — yield of 83%.

The mercaptonorbornylsilane had the following physical properties:

b.p. 80°/0.2 mm Hg; $\eta^{25} = 1.4827$; theoretical molecular weight 248.3; molecular weight found 260; Elemental Analysis = Calculated for $C_{10}H_{20}O_3SSi$: C, 48.37; H, 8.12; Si, 11.30; S, 12.91. Found C, 49.38; H, 7.80; Si, 11.44; S, 13.03.

Titration with standard iodine solution showed the presence of one —SH group. The IR and NMR spectra are in agreement with the proposed molecular structure of

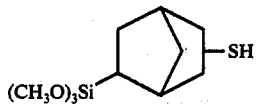

EXAMPLE IV

Into a 100 ml three-necked flask were charged 39.3 grams of

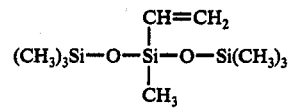

(MD'M) and 10.3 grams of cyclopentadiene. The mixture was heated and stirred to reflux. Reaction temperature rose to 150° C. after 8 hours. Vapor phase chromatographic analysis showed most of MD'M had been reacted. Distillation yielded 37 grams of product, b.p. 71°/1.4 mm Hg. The product was identified as

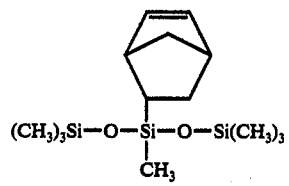

by its infrared and NMR spectra. A yield of 75% and a refractive index, $\eta^{25} = 1.4376$, were recorded.

EXAMPLE V

Synthesis of

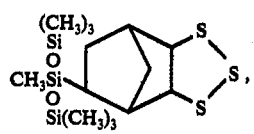

as an example of a polysiloxane containing a norbornanyl trithiane structure.

Into a 100 ml, 3-necked flask equipped with a stirrer, a thermometer and a condenser were charged 22.3 grams of

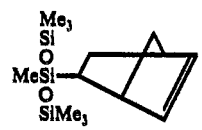

6.83 grams of sulfur, 51.2 grams of N,N-dimethyl formamide solvent and 0.041 gram of ammonia. The contents were stirred and heated to 110° C. for 2 hours and 30 minutes. The contents turned into a dark, homogeneous reaction mixture. The solvent, N,N-dimethyl formamide, was stripped under vacuo. The recovered N,N-dimethyl formamide (50.5 grams) was essentially quantitative. A portion of the crude reaction mixture, 25.7 grams, was trap-to-trap distilled under high vacuum to give 24.3 g. light yellow liquid product. Yield was 93%. The product was identified as

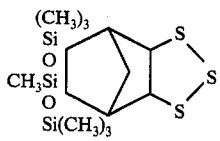

by its infrared and nuclear magnetic resonance spectra and by elemental analysis.

Calculated for $C_{14}H_{30}O_2Si_3S_3$: C, 40.94; H, 7.36; S, 23.42; Si, 20.50; Found C, 40.12; H, 7.36; S, 24.92; Si, 20.55. A refractive index, $\eta^{25} = 1.5122$, and a viscosity of 72 centistokes were recorded.

EXAMPLE VI

Synthesis of trimethoxy-2-(5-norbornenyl)ethyl silane,

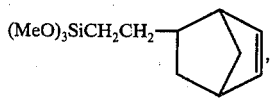

as an example of a silicon hydride to unsaturated organic compound containing a norbornenyl structure.

Into a 1-liter three-necked flask equipped with a stirrer, a thermometer and a condenser were charged 364 grams 2-vinyl-5-norbornene,

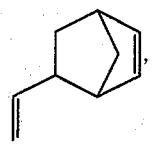

398 grams of trimethoxysilane, $HSi(OCH_3)_3$, and 50 parts per million of platinum in the form of chloroplatinic acid. The contents were heated slowly. An exothermic reaction occurred at about 90° C. and the reaction temperature rose to 110° C. for a total of 5 hours reaction. Distillation of the reaction mixture yielded a 520 grams fraction having a boiling point of 85° C. at 0.17 mm Hg. The product was identified by its infrared and NMR spectra as

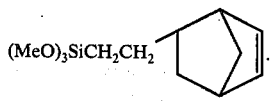

A yield of 84%, refractive index $\eta^{25} = 1.4546$ and a viscosity of 8.6 centistokes at room temperature were recorded.

Employing the same procedure, $HSi(OCH_3)_3$ is added to

to yield

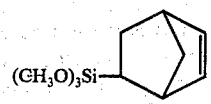

and $HSi(OCH_3)_3$ is added to bicyclopentadiene,

to yield a mixture of

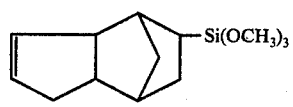

and

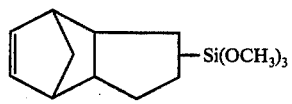

(viscosity, 9 centistokes at room temperature). Addition by the same procedure of $HSi(OMe)_3$ to ethylidenenorbornene,

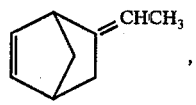

yields a mixture of

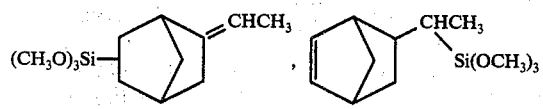

and

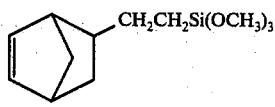

(viscosity of 8 centistokes at room temperature).

EXAMPLE VII

Into a 300-ml rocking autoclave were charged 91.3 grams of

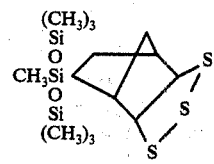

(from example V), and 0.65 gram (0.7 wt %) of rhenium heptasulfide catalyst. The reactor was purged with dry nitrogen and then pressurized with 1800 psi of hydrogen gas. The contents were heated for 18 hours. The excess gas was vented and the crude reaction mixture was collected. The reaction crude was distilled under vacuo. A fraction, 64.5 grams, b.p. 140° C. at 0.1 mm Hg was collected. IR and NMR spectra of the product fraction showed it was

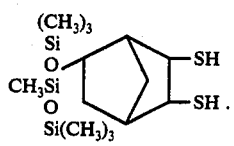

Yield was 76% based on the starting norbornenyl compound. Elemental analysis on the distilled product proved the composition of the structure proposed.

Calculated for $C_{14}H_{32}O_2S_2Si_3$: C, 44.17; H, 8.47; S, 16.85; Si, 22.11; Found C, 43.85; H, 8.20; S, 17.13; Si, 20.45. The refractive index, $\eta^{25} = 1.4850$ and viscosity, 25 centistokes at room temperature, were also recorded.

EXAMPLE VIII

The reaction of

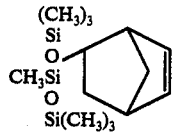

with hydrogen sulfide was carried out in a 300 ml rocking autoclave.

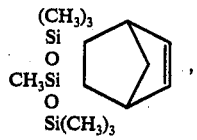

(108 grams), Vazo (azobisisobutyronitrile) catalyst (0.25 gram) and an excess of H₂S (50 grams) were charged into the high pressure reactor. The contents were heated to 100° C. for 2½ hours. After cooling to room temperature, excess H₂S was vented and destroyed. The colorless reaction mixture was collected and distilled under vacuo. A fraction, which weighed 100 grams was collected at 100° C. at 0.2 mm Hg. Infrared and NMR spectra of the distilled product were in agreement with the molecular structure of

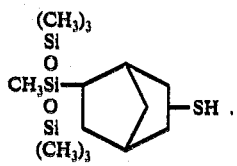

A viscosity of 7 centistokes at room temperature was recorded.

As described above in the Examples, the trithiane substituted cycloaliphatic silicon compound is produced by the reacting elemental sulfur with the corresponding unsaturated cycloaliphatic silicon compound in the presence of a strong base catalyst. Useful catalysts for effecting that reaction include, for example, ammonia, amines such as primary, secondary and tertiary amines (e.g., alkyl amines, aryl amines, cycloaliphatic amines such as methyl amine, dimethyl amine, trimethyl amine, ethyl amine, diethyl amine, triethyl amine, pyridine, morpholine, aniline, triphenyl amine, diphenyl amine, and the like), and the like. The reaction is typically carried out in the presence of a very polar solvent. Suitable solvents which one may employ in effecting this reaction include, by way of example, N,N-dimethyl formamide, N,N-dimethyl acetamide, dimethyl sulfoxide, tetrahydrofuran, dioxane, and the like. Also, one may add to the solution, in lesser quantities, and as a diluent, such solvents as aromatic hydrocarbon solvents. Illustrative of such solvents are, for example, toluene, benzene, xylene, and the like. The amount of the ammonia or amine catalyst one employs may range from as low as about 0.1 weight percent to about 2 weight percent, based upon the weight of the reactants employed. In determining this weight percent for the ammonia or amine catalyst, one excludes the amount of solvent employed in carrying out the reaction. The reaction may be carried out over a temperature of about 50° to about 200° C., though preferably, the reaction is effected at about 75° C. to about 150° C.

The conversion of the trithiane substituted cycloaliphatic silicon compound to the dimercaptan may be effected under general hydrogenation conditions. Suitable hydrogenation catalysts include sulfide catalysts such as cobalt sulfide, cobalt polysulfide, nickel sulfide, nickel polysulfide, titanium sulfide, titanium polysulfide, rhenium sulfide, rhenium polysulfide, molybdenum sulfide, molybdenum polysulfide, and the like. Such catalysts are typically in the solid state and are used as fine powders which are kept in suspension during the hydrogenation reaction. The temperature of the reaction may range from as low as about 50° C. to about 200° C., preferably at about 85° C. to about 185° C. under pressures which typically exceed about 15 pounds per square inch gauge. The reaction can be carried out in a rocking autoclave or other types of pressure vessels which provide good distribution of the catalyst in the reaction sysem.

When reacting the unsaturated cycloaliphatic silicon compounds with hydrogen sulfide, as characterized above, such reaction is typically effected in the presence of a free radical catalyst for thiolation reactions. The usual catalysts for effecting such reactions may be employed herein. Illustrative of such catalysts are, for example, the conventional bisazo addition catalysts as illustrated by azobisisobutyronitrile, and the conventional organic peroxides, such as, for example, tertiarybutyl hydroperoxide, di-tertiarybutyl peroxide, benzoyl peroxide, and the like. The reaction temperature is dependent upon the decomposition temperature of the peroxide which is selected as well as the rate of reaction that is desired. Usually, one employs the optimum decomposition temperatures of the particular peroxide employed or the azo catalyst utilized. Usually the operating temperature is about 50° C. to about 150° C., though lower and higher temperatures may be employed if more or less reactive free radical catalysts are employed. This reaction can be carried out in the absence of a solvent, though if one is employed one normally chooses an inert solvent such as the hydrocarbon solvents described above.

What is claimed is:
1. Sulfur substituted norbornyl substituted compounds characterized by having present therein the structure:

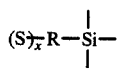

wherein the free valences of the silicon atom are bonded to one or more monovalent hydrocarbon groups and hydrolyzable groups, R is one of the polyvalent cycloaliphatic hydrocarbon radicals characterized as follows:

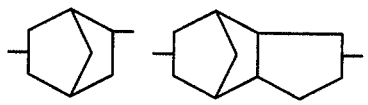

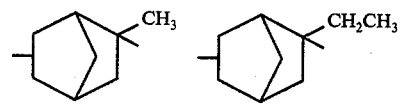

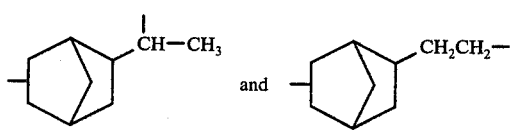

$x$ has the value of 2 or 3; provided that when $x$ is 2 each sulfur atom is bonded to hydrogen to form a mercaptan, and when $x$ is 2, the two mercaptans are attached to separate carbon atoms and such carbon atoms are adjacent to one another, and when $x$ is 3, the sulfur atoms form a trisulfide wherein each sulfur atom is bonded to another sulfur atom and the terminal valences of the trisulfide are bonded to vicinal carbon atoms of R.

2. A compound as defined in claim 1, wherein the free valences of the silicon atom are bonded only to hydrolyzable groups.

3. A compound as defined in claim 2, wherein said hydrolyzable groups are alkoxy.

4.

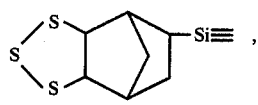

wherein the free valences of the silicon atom are bonded to alkoxy.

5.

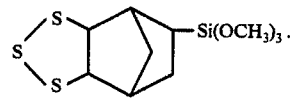

6.

wherein the free valences of the silicon atom are bonded to alkoxy.

7.

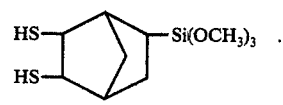

8.

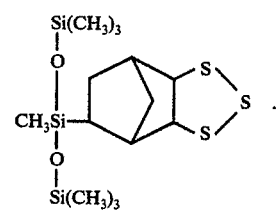

9.

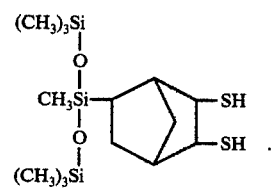

10.

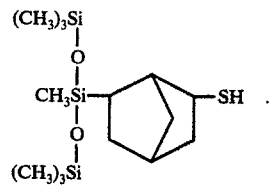

* * * * *